US009523086B2

(12) United States Patent
Dafforn et al.

(10) Patent No.: US 9,523,086 B2
(45) Date of Patent: Dec. 20, 2016

(54) PROTEIN EXTRACTION

(75) Inventors: Timothy Richard Dafforn, Kenilworth (GB); Owen Robert Tyrynis-Thomas, Birmingham (GB)

(73) Assignee: The University of Birmingham, Birmingham (GB)

(*) Notice: Subject to any disclaimer, the term of this patent is extended or adjusted under 35 U.S.C. 154(b) by 15 days.

(21) Appl. No.: 14/116,584

(22) PCT Filed: May 9, 2012

(86) PCT No.: PCT/GB2012/000423
§ 371 (c)(1),
(2), (4) Date: Mar. 10, 2014

(87) PCT Pub. No.: WO2012/153089
PCT Pub. Date: Nov. 15, 2012

(65) Prior Publication Data
US 2014/0199751 A1 Jul. 17, 2014

(30) Foreign Application Priority Data
May 9, 2011 (GB) .................................. 1107737.7

(51) Int. Cl.
| *A61K 38/10* | (2006.01) |
| *A61K 49/00* | (2006.01) |
| *A61K 31/74* | (2006.01) |
| *C08G 69/48* | (2006.01) |
| *C12N 9/28* | (2006.01) |
| *C12N 1/06* | (2006.01) |
| *C12P 21/00* | (2006.01) |
| *A61P 29/00* | (2006.01) |
| *C08L 77/00* | (2006.01) |

(52) U.S. Cl.
CPC ............... *C12N 9/2417* (2013.01); *C12N 1/06* (2013.01); *C12P 21/00* (2013.01)

(58) Field of Classification Search
CPC ............. A61K 38/10; A61K 47/48207; A61K 47/48215; A61K 47/48246; A61K 49/00; A61K 31/74; C08G 83/004; C08G 69/48; C12N 9/2417; C12N 1/06; C12P 21/00; A61P 29/00; C08L 77/00
USPC .......... 424/9.1; 525/420, 432; 514/152, 177, 514/180, 210.05, 21.4
See application file for complete search history.

(56) References Cited

U.S. PATENT DOCUMENTS

| 4,497,730 A | 2/1985 | Ames et al. |
| 4,595,658 A | 6/1986 | Zinder et al. |
| 5,700,665 A | 12/1997 | Legoux et al. |
| 6,436,905 B1 | 8/2002 | Tonge et al. |
| 8,754,168 B2 | 6/2014 | Dafforn et al. |

FOREIGN PATENT DOCUMENTS

| CN | 1227873 A | 9/1999 |
| GB | 2426703 A | 6/2006 |
| WO | 2011004158 A1 | 1/2011 |

OTHER PUBLICATIONS

Nossal et al. 1966. The Release of Enzymes by Osmotic Shock from *Escherichia coli* in Exponential Phase. The Journal of Biological Chemistry, vol. 241, No. 13, Issue of Jul. 10 1966, pp. 3055-3062.*
Nguyen. M.T (henceforth Nguyen, 2006. The effect of temperature on the growth of the bacteria *Escherichia coli* DH5α. Saint Martin's University Biology Journal May 2006, vol. 1, pp. 87-94.*
Paal et al (2009. A novel Ecotin-Ubiquitin-Tag (ECUT) for efficient, soluble peptide production in the periplasm of *Escherichia coli*. doi: 10.1186/1475-2859-8-7, Microbial Cell Factories vol. 8:, p. 7.*
Rajesh, et al.. "Production of membrane proteins without cells or detergents"; New Biotechnology (2011) 28: 250-254.
Jamshad, et al., Biochemical Society Annual Symposium No. 78 (2011).
Slobodyanikova, et al., "Stabilization of Bacillus subtilis proteases in solution", Applied Biochemistry and Microbiology 15 (1979): 412-418.
Knowles T J. et al. "Membrane proteins solubilized intact in lipid containing nanoparticles bounded by styrene maleic acid copolymer", Journal of the American Chemical Society. vol. 131. No. 22 (Jun. 10, 2009), pp. 7464-7485.
Yu-pin Lin; "Over-expression and Biophysical Characterisation of Membrane Proteins Solubilised in a Styrene-Maleic Acid Polymer (Thesis)", Feb. 2011, pp. 6-197.
British Search Report issued Aug. 31, 2011 in connection with related British Patent Appl. No. GB1107737.7.
PCT Search Report issued Aug. 9, 2012 in connection with related PCT Application No. PCT/GB2012/000423.

* cited by examiner

*Primary Examiner* — Debbie K Ware
*Assistant Examiner* — Kailash C Srivastava
(74) *Attorney, Agent, or Firm* — Berliner & Associates

(57) ABSTRACT

A method for releasing the content of the periplasmic space of bacterial cells is provided, which comprises incubating the bacterial cells in a solution containing styrene maleic acid copolymer (SMA). Also provided is a method of preparing a substantially pure sample of recombinant polypeptide. The methods find application in the recovery of materials, such as proteins, from bacterial cells.

18 Claims, 12 Drawing Sheets

PROTEIN EXTRACTION

Figure 1:
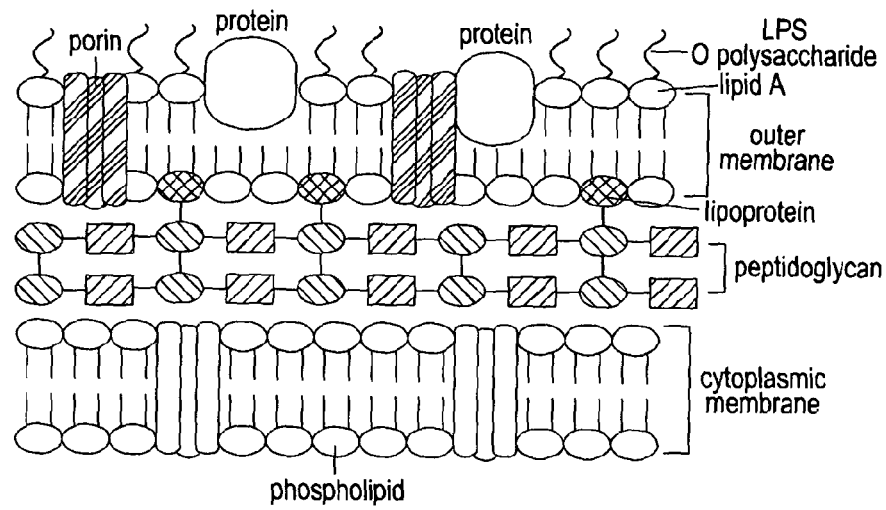

The present invention concerns methods for improving the recovery of materials from bacterial cells.

The bioprocessing industry has undergone huge growth in the fields of biotherapeutics and biotechnology, and in recent years there has been a large increase in the amount of biopharmaceutical products prepared using such methods (e.g. vaccines and monoclonal antibodies). Recent data has shown that about 44% of all pharmaceutics are biopharmaceutical products.

The technique of bioprocessing consists of a number of steps. A host cell is prepared which can synthesise the biopharmaceutical product of interst. Following fermentation of the host cells (the 'bioreactor step'), the product is typically secreted and/or extracted from the cells, the 'product release step'. The specific products then need to be purified by downstream processing, such as filtration, centrifugation and various chromatography steps. Such methods can be used to prepare biopharmaceutical products for therapeutic applications. The product release step and subsequent recovery of such products are key stages in the bioprocessing technique.

For a variety of reasons the host cell of choice for the production of biopharmaceuticals, and other recombinant proteins of interest, is *Escherichia coli*. *E. coli* is a Gram negative bacterium. These cells can be grown easily, and contain a relatively simple genome. The genetics of these cells can be easily manipulated which makes them important in the fields of microbiology, biotechnology and bioprocessing.

As well as the usual cell membrane, Gram-negative bacteria such as *E. coli* contain an additional outer membrane containing lipopoysaccharides and lipoproteins as well as phospholipids and membrane proteins. The lipopolysaccharides consist of a covalently-bound lipid A molecule linked to an O-polysaccharide, which gives the outer membrane a strong negative charge. There is a space between the inner and outer membranes, termed the periplasmic space, which in Gram-negative bacteria contains the thin peptidogycan matrix layer—which is known to give a structural function in the cell wall. The peptidoglycan matrix layer is composed of two sugars, N-acetyl muramic acid and ($\beta$1-4) N-acetylglucosamine, which alternate in the structure of the layer. The N-acetyl muramic acid monomers contain a side link with a peptide chain consisting of several amino acid residues. This peptide chain has the potential to bind another peptide chain in another N-acetyl muramic acid monomer, in order that the peptidoglycan can form a 'mesh-like' layer. This peptidoglycan layer also contains pores or openings, which can be large enough for proteins to pass through.

In organisms such as *E. coli* some proteins can be transported out of the cytoplasm and into various other membrane compartments including the periplasmic space. Proteins destined for export from the cytoplasm contain a 'signal peptide', which is an extension of the N-terminal of the protein. These 'signal peptides' contain three conserved regions; a N-terminal region, a core region and a C-terminal region. Once the protein has reached its required destination, the signal peptide can be cleaved from the mature protein by an enzyme called signal peptidase, therefore releasing the mature polypeptide in the designated compartment of the cell membrane (e.g periplasm).

The translocation of proteins to the periplasmic space has been exploited by the bioprocessing industry to aid the recovery of biopharmaceutical products. This is in order to minimise the amount of released contaminants from the cytoplasm, and also to avoid the micronization of cell.

There are a number of existing methods in the literature for the release of periplasmic proteins, but none are ideal. Chemical treatment of bacterial cells using detergents (such as Triton X-100) and chloroform leads to increased permeabilization of the outer membrane, but also leads to low protein purity therefore increasing the costs related to downstream processing. The treatment of *E. coli* cells with anionic surfactants can also lead to the release of a number of periplasmic proteins, including penicillin acylase. The outer membrane can also be permeabilized by treatment with glycine to release the periplasmic contents of the bacteria including $\alpha$-amylase, giving a 70-80% recovery of this protein. The technique of osmotic shock has also shown promise in the release of penicillin acylase from the periplasm of *E. coli* cells. Whilst these methods have shown relative success on a small-scale in the laboratory, the step-up to make these techniques viable on a larger-scale has shown little promise.

The most efficient method of periplasmic protein release to date uses EDTA (ethylenediaminetetraacetic acid) in combination with the lysozyme enzyme. EDTA leads to the chelation of divalent cations, such as $Ca^{2+}$, which causes membrane destabilization allowing lysozyme access to break down the peptidoglycan matrix present in the periplasm. This allows release of a greater amount of periplasmic proteins, such as $\alpha$-amylase. Even though this method leads to a increased periplasmic release during small-scale laboratory experiments it has proved to be an expensive method when scaled up for use in larger volumes in industry.

Therefore, there is still a need to develop an efficient, yet inexpensive method in order to release the periplasmic contents of Gram-negative bacteria.

The present inventors decided to develop a new periplasmic protein release method in order to achieve a more efficient way of extracting periplasmically targeted therapeutic proteins. They have surprising found that styrene maleic acid (SMA) copolymer can specifically disrupt the outer membrane of bacterial cells in order to release the content of the periplasm, while not disrupting the inner membrane, thus avoiding the presence of contaminant proteins from the cytoplasm in the protein samples.

Accordingly a first aspect of the invention provides a method for releasing the content of the periplasmic space of bacterial cells comprising incubating bacterial cells in a solution containing styrene maleic acid copolymer (SMA).

The inventors decided to investigate whether styrene maleic acid (SMA) can be used to extract periplasmic proteins from cells. They have surprisingly found that SMA specifically disrupt the outer membrane of bacterial cells but not the inner membrane. Therefore, SMA can be used to selectively extract periplasmic proteins without the release of contaminant proteins from the cytoplasm. The extraction method is simple to perform and can be readily scaled up to a large-scale bioprocessing process. The method significantly reduces the costs involved since there are fewer purification steps in downstream processing.

While SMA has previously been used isolate and preserve transmembrane proteins, and for the delivery of therapeutic agents, until the present invention it had not been disclosed or suggested that SMA could be used to release the content of the periplasmic space.

In practice, the method of the invention can be readily used to selectively release the contents of the periplasmic space into solution. Specific components of the periplasmic space, for example recombinant protein for industrial uses, can then be readily isolated from the solution. Therefore the present invention has clear beneficial and industrial applications.

The method of the first aspect of the invention includes a step of incubating bacterial cells in a solution containing styrene maleic acid copolymer (SMA).

Bacterial species can generally be divided into "gram-positive" and "gram-negative" species, the difference being specifically attributable to the retention of particular dyes that depend on the structural differences of their bacterial cell walls.

The bacterial cells that can be used in the method can be any suitable cells. Preferably the bacterial cells are a Gram-negative bacterial species, preferably *E. coli, Salmonella* sp., *Pseudomonas fluorescens, Shigella* sp., *Yersinia* sp. or *Klebsiella* sp. Such bacteria species are well known in the art. Bacterial cells for those species can be readily obtained, either from commercial suppliers or biological material collections such as the ATCC (http://www.lgcstandards-atcc.orq/).

As is well known in the field, mutated derivatives of such Gram-negative bacterial species have also been prepared that improve the quality and/or quantity of the amount of protein produced. They are therefore also considered to be examples of bacterial cells that can therefore be used in this aspect of the invention.

Methods of preparing bacterial cells for use in the method of the invention are well known in the art. As outlined further below, in some instances the bacterial cell will contain recombinant polypeptides. Methods of culturing such cells above for a sufficient time and under appropriate conditions in a culture medium so as to obtain expression of the recombinant polypeptide are well known in the art. An example is provided herein of one such method in the accompanying examples section.

The method of the first aspect of the invention uses a solution containing styrene maleic acid copolymer (SMA).

In some embodiments, providing a copolymer of styrene and maleic acid comprises providing a copolymer of styrene and maleic anhydride, and hydrolysing the maleic anhydride to maleic acid. Copolymers of styrene and maleic anhydride are available from Sartomer Company Inc., Exton Pa., USA under the trade names SMA® 2000 and SMA® 3000. Suitable hydrolysis methods are known in the art.

As way of example, the following protocol can be used to prepare a solution of SMA that can be used in the method of the first aspect of the invention.

A solution of SMA 2000P (obtained from Sartomer) and 1M sodium hydroxide (10% w/v) was mixed gently overnight in a round bottom flask on a magnetic stirrer at room temperature (25 g of SMA 2000P dissolved in 250 ml of NaOH). A few anti-bumping granules were then added to the round bottom flask which was then placed on a heating mantle with a condenser attached. The SMA/NaOH solution was allowed to reach boiling point. After boiling, the heat was turned down and the solution was allowed to reflux for 2 hours, before being transferred to a cold room for 2 days. These processes were carried out in a fume cupboard. After this cooling period, the volume was measured and the percentage content of SMA was calculated, before being aliquotted into 50 ml falcon tubes and stored at −70° C.

When used, preferably the solution contains 50 mM TRIS pH 8.0 at 0.5M NaCl.

In some embodiments, providing a copolymer of styrene and maleic acid wherein the styrene:maleic acid ratio is between 0.5:1 and 10:1 comprises providing a copolymer of styrene and maleic acid wherein the styrene:maleic acid ratio is between 1:1 and 5:1. In some further embodiments, the styrene:maleic acid ratio is between 1.5:1 and 4:1, or between 2:1 and 3:1.

It will be understood that, due to the nature of polymerisation processes, such monomer ratios are bulk averages, and are not to be taken as descriptive of a particular molecular structure having defined arrangements of monomers.

Nevertheless, in general it is to be expected that the monomer types are distributed throughout the copolymer.

In some embodiments, providing a copolymer of styrene and maleic acid comprises providing a copolymer of styrene and maleic acid having a molecular weight of between 3000 Da and 120000 Da. In some further embodiments, the copolymer has a molecular weight of between 5000 Da and 15000 Da. In some still further embodiments, the copolymer has a molecular weight of between 7000 and 10000 Da.

The present inventors have investigated the range of concentrations of SMA that can be used to release the content of the periplasmic space. They have shown that at least a range of approximately 0.5-4.5% of SMA in solution can be successfully used for that purpose. In an embodiment, the concentration of SMA is approximately 0.5%-10%, 1%-7% or 1.5%-5%. In a further embodiment, the concentration of SMA is approximately 2-2.5%.

The present inventors have investigated the temporal effect of SMA on the release the content of the periplasmic space. They have shown that at least a range of approximately 15 minutes to 6 hours incubation time can be successfully used for that purpose. Preferably the incubation time is approximately 2 hours. Also preferably the bacterial cells are incubated with the SMA at approximately 37° C.

Accordingly therefore from the information provided herein a preferred embodiment of the first aspect of the invention is where the method comprises the steps of: (i) preparing a population of bacterial cells; (ii) suspending the bacterial cells in a solution containing SMA having a styrene:maleic acid ratio of approximately 2:1 and at a concentration of approximately 2-2.5%; and (ii) incubating the bacterial cells in the solution for approximately 2 hours at approximately 37° C.

The inventors have also noted that the presence of EDTA (1 mM) in the solution with the SMA leads to a significant decrease in the materials released from the periplasmic space. Hence a preferred embodiment of the method of the invention is wherein the solution is substantially free of EDTA.

The present inventors also investigated the effect of an osmotic shock on the efficiency of release of the content of the periplasmic space. As shown in the accompanying examples, the use of an osmotic shock caused in increase in the materials released from the periplasmic space. Hence a preferred embodiment of the method of the invention is where the method comprises exposing the cells to an osmotic shock. Preferably the osmotic shock is performed following incubation of the cells with the SMA solution.

The method of the invention can be used to release the content of the periplasmic space. The composition of the periplasm can include oligosaccharides, amino acids, peptides, and various small molecules. The operator the method of the invention can use the method to release these components from the cells, which can subsequently be further purified from the solution using methods well known in the art.

In a preferred embodiment of the invention the bacterial calls express periplasmically targeted recombinant polypeptide. Methods of directing recombinant polypeptide to the periplasm are well known in the art. Accordingly therefore the method of the invention can be used as part of large-scale bioprocessing process to selectively release the contents of the periplasmic space, including such recombinant polypeptide into solution for subsequent purification.

Hence a further embodiment of the invention is wherein the method further comprises recovering at least a proportion of one component of the periplasmic space from the solution. A further embodiment of the invention is wherein the periplasmic space contains recombinant polypeptide. A further embodiment of the invention is wherein the method further comprises recovering at least a proportion of recombinant polypeptide from the solution.

Recombinant polypeptides can be readily isolated from the solution using standard techniques known in the art, including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography.

Where it is desired to isolate specific recombinant polypeptides which has been genetically engineered to include a purification tag (such as multiple histidine residues, or a glutathione S-transferase enzyme), such polypeptides can be purified by any method appropriate to the particular purification tag used, such as for example affinity chromatography. Other protein purification techniques well known in the art may also be used, as will be readily appreciated by the person skilled in the art.

A further aspect of the invention provides a method of preparing a substantially pure sample of recombinant polypeptide, the method comprising: (i) preparing a population of bacterial cells comprising the recombinant polypeptide; (ii) suspending the bacterial cells in a solution containing SMA having a styrene:maleic acid ratio of approximately 2:1 and at a concentration of approximately 2-2.5%; and (ii) incubating the bacterial cells in the solution for approximately 2 hours at approximately 37° C.; (iv) recovering the recombinant polypeptide from the solution.

For the avoidance of doubt, embodiments of the first aspect of the invention also apply to the method of this aspect of the invention.

Hence as way of example the following protocol can be used as an embodiment of the methods of the invention.

A population of bacterial cells is grown under appropriate culture conditions. If the bacterial cells synthesise a recombinant periplasmically targeted polypeptide, then the culture conditions are such to facilitate the expression and accumulation of such a polypeptide. The cells are then harvested using standard laboratory methods (for example, centrifugation) and suspended in a solution containing SMA having a styrene:maleic acid ratio of approximately 2:1 and at a concentration of approximately 2-2.5%. The cell suspension is incubated for 2 hours at approximately 37° C. The cells are then removed from the solution using standard laboratory methods (for example, centrifugation). The resulting solution contains the content of the periplasmic space. Specific components of the periplasmic space can then be isolated using, for example, affinity purification means as known in the art.

A further aspect of the invention provides the use of styrene maleic acid copolymer (SMA) for releasing the content of the periplasmic space.

A further aspect of the invention provides a kit of parts comprising: (i) a solution comprising styrene maleic acid copolymer (SMA); and (ii) a manual of operation. Preferably the kit of parts of further comprises one or more additional components including protein purification columns or resins.

The manual of operation can include information concerning, for example, preferred incubation conditions and reaction procedures as provided herein, and other such information as appropriate.

The invention is now described by reference to the following, non-limiting, figures and examples.

FIGURE LEGENDS

FIG. 1: Cell wall structure of a Gram-negative bacterium

Figure 2:
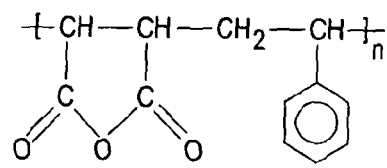

FIG. 2: Styrene maleic acid (SMA)

Figure 3:
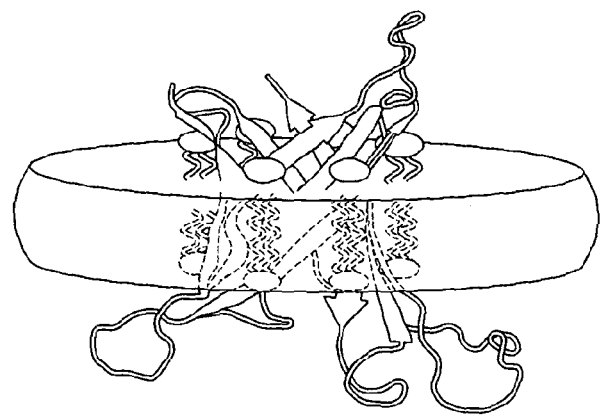

FIG. 3: The formation of lipid nanodisks by SMA in order to preserve and isolate transmembrane proteins.

Figure 4:
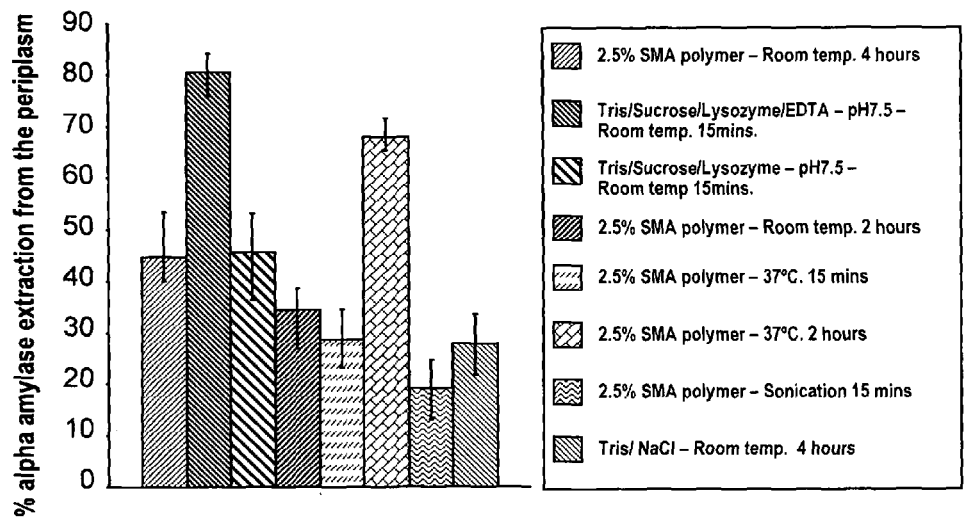

FIG. 4: The effect of various conditions on the periplasmic release of α-amylase.

Figure 5:
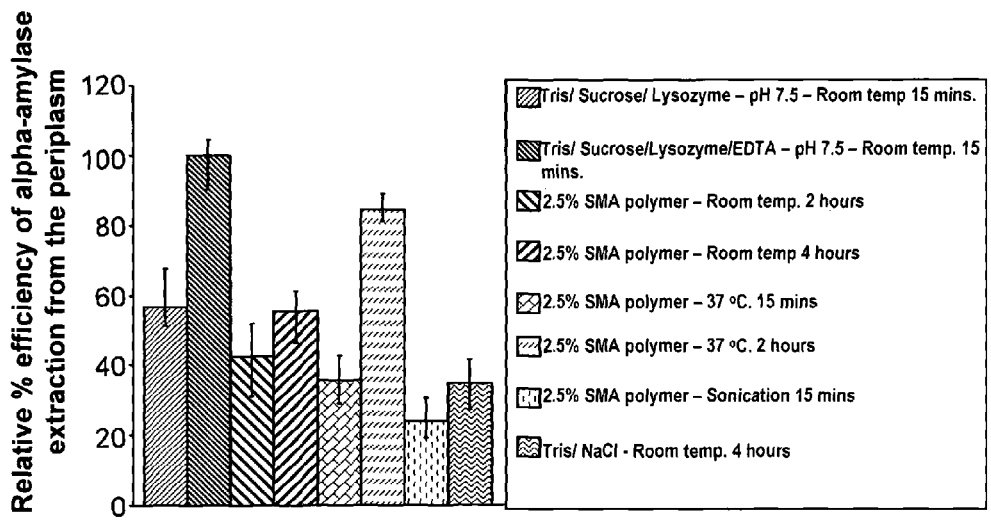

FIG. 5: The efficiency of various periplasmic release methods from E. coli bacterial cells.

Figure 6:
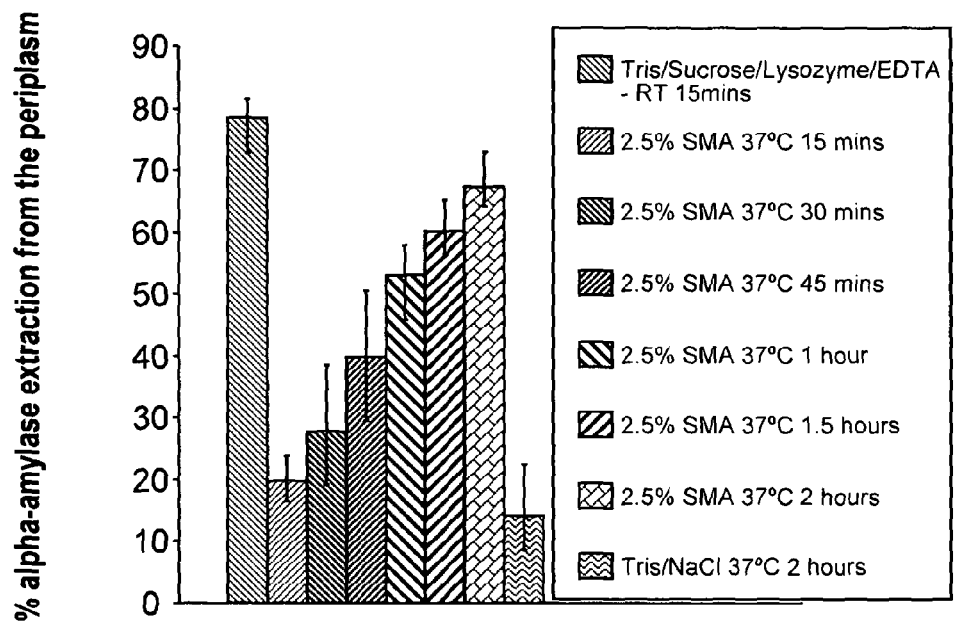

FIG. 6: The effect of an enlonged 37° C. incubation time upon the periplasmic release of α-amylase by SMA.

Figure 7:
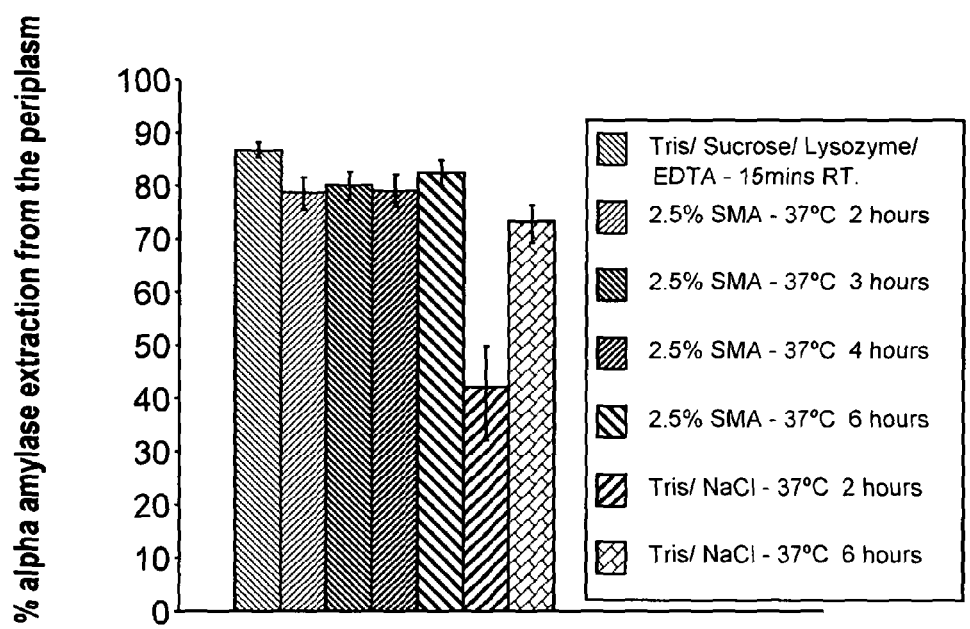

FIG. 7: The effect of a longer incubation time upon the periplasmic release of α-amylase by SMA.

Figure 8:
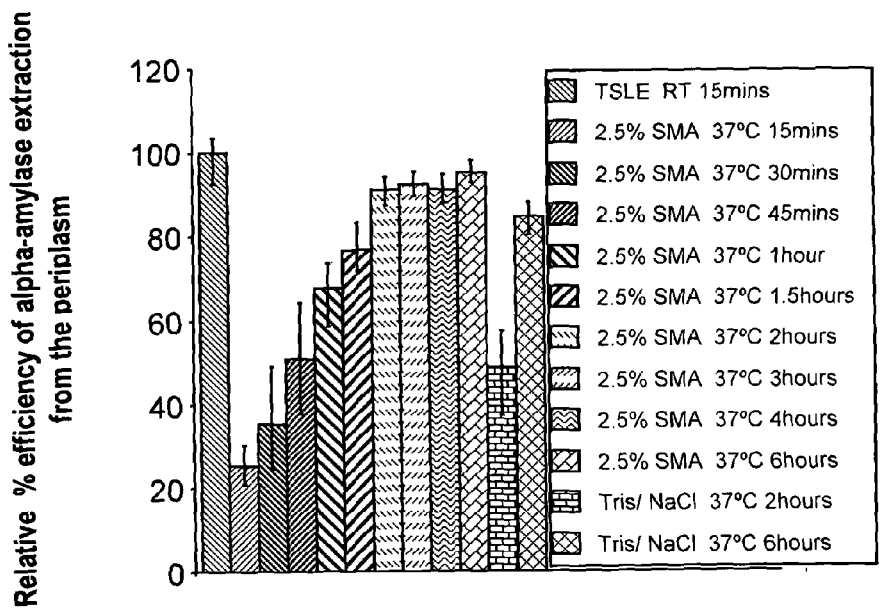

FIG. 8: The efficiency of various SMA periplasmic release methods from E. coli.

Figure 9:
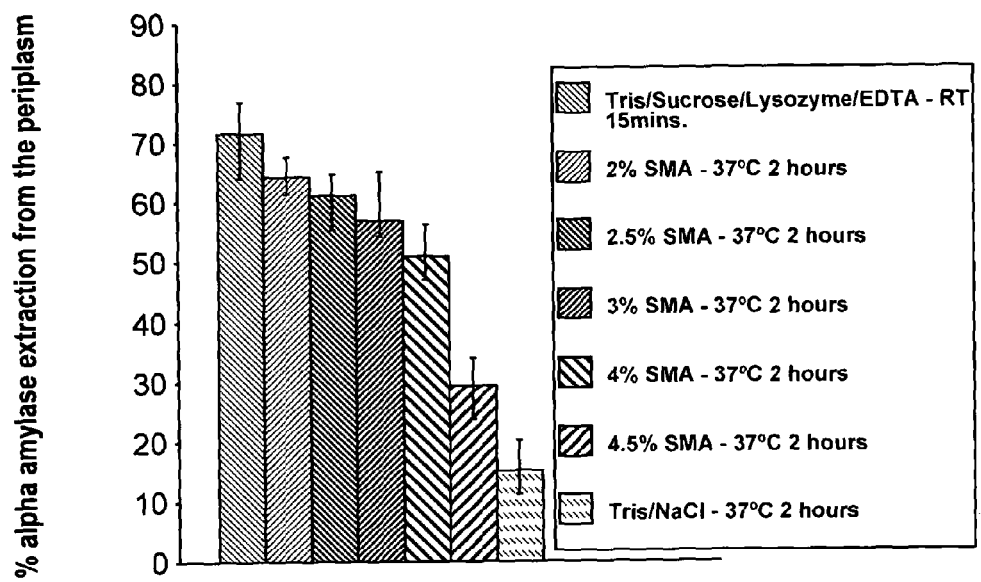

FIG. 9: The effect of increasing concentrations of SMA lipid polymer on the release of α-amylase from the periplasm.

Figure 10:
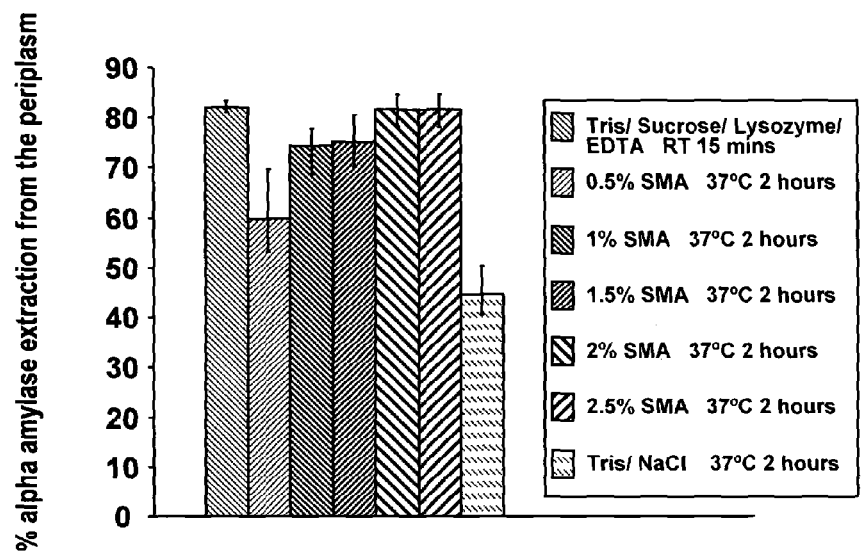

FIG. 10: The effect of varying concentrations of SMA lipid polymer on the release of α-amylase from the periplasm.

Figure 11:
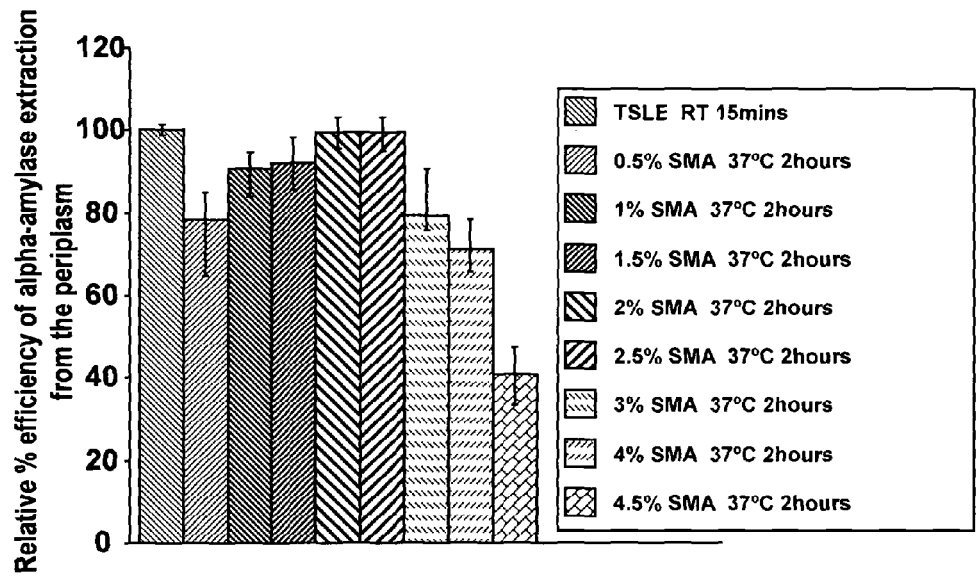

FIG. 11: The efficiency of various SMA periplasmic release methods from E. coli.

Figure 12:
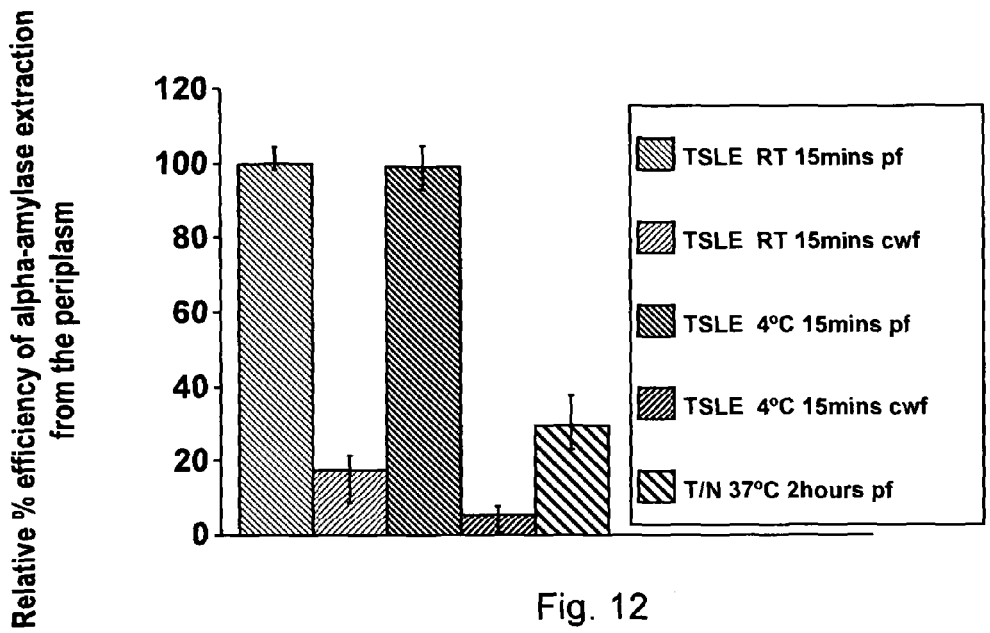

FIG. 12: The effect of a change in temperature on the mode of action of the optimal TSLE release method.

Figure 13:
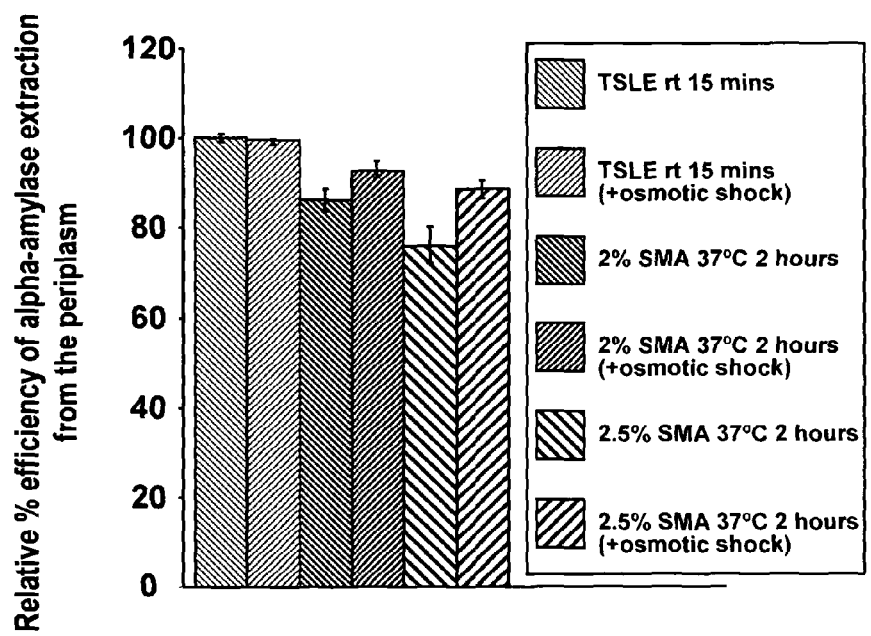

FIG. 13: The effect of an osmotic shock on various periplasmic release methods.

Figure 14:
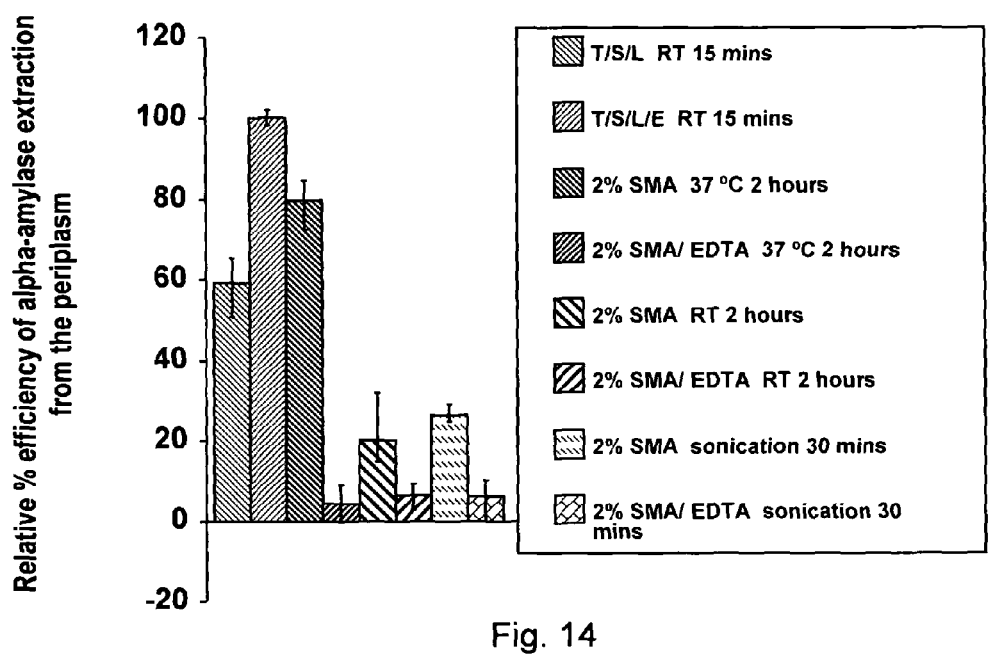

FIG. 14: The effect of EDTA on various treatments of periplasmic α-amylase release.

Figure 15:
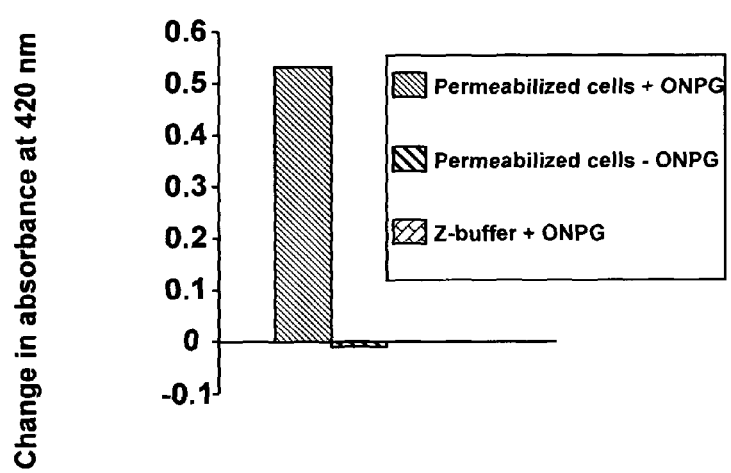

FIG. 15: Initial assay to detect the presence of β-galactosidase in these E. coli cells.

Figure 16:
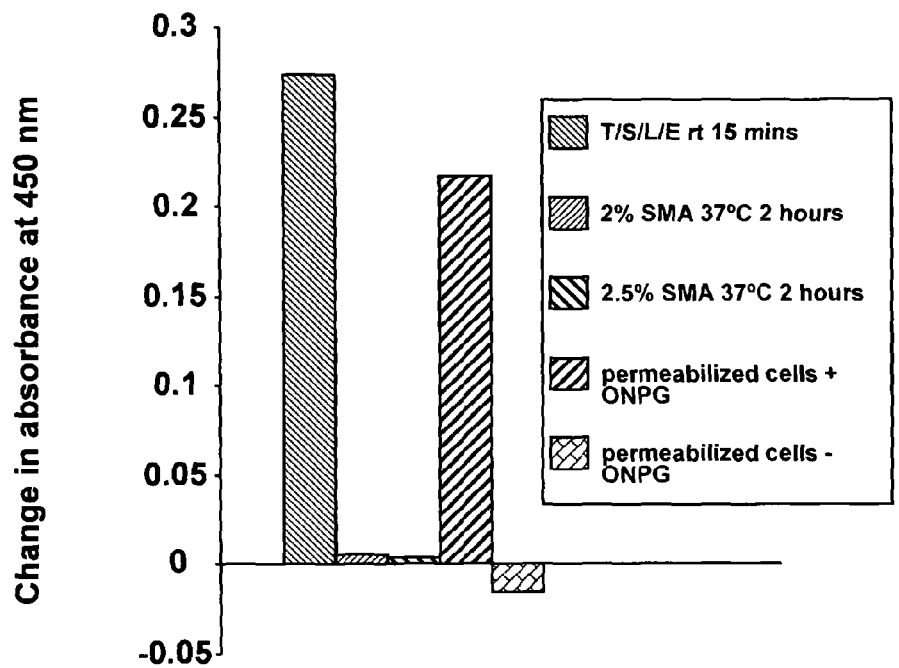

FIG. 16: The effect of various conditions on the release of β-galactosidase.

Figure 17:
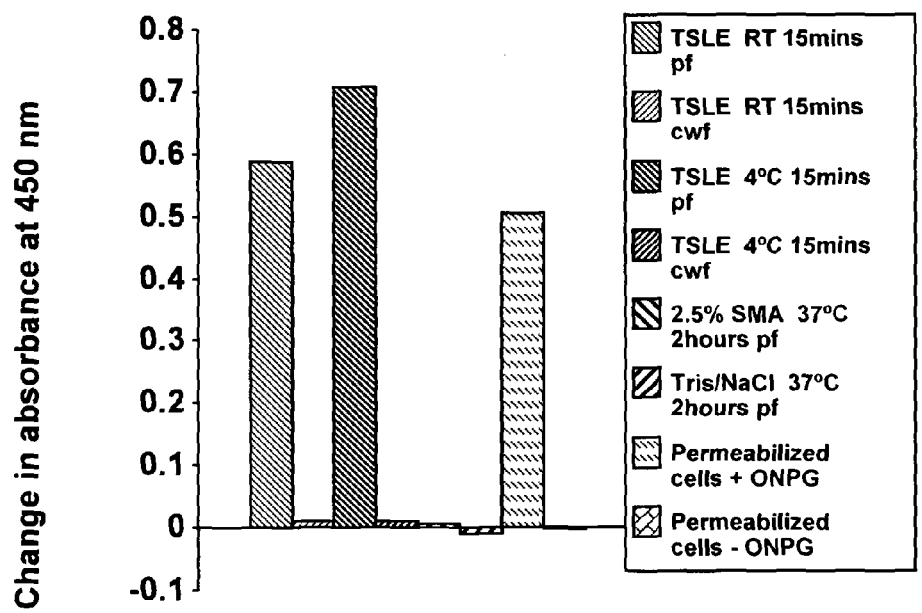

FIG. 17: The effect of a various number of condtions on the extraction of β-galactosidase from E. coli cells.

Figure 18:
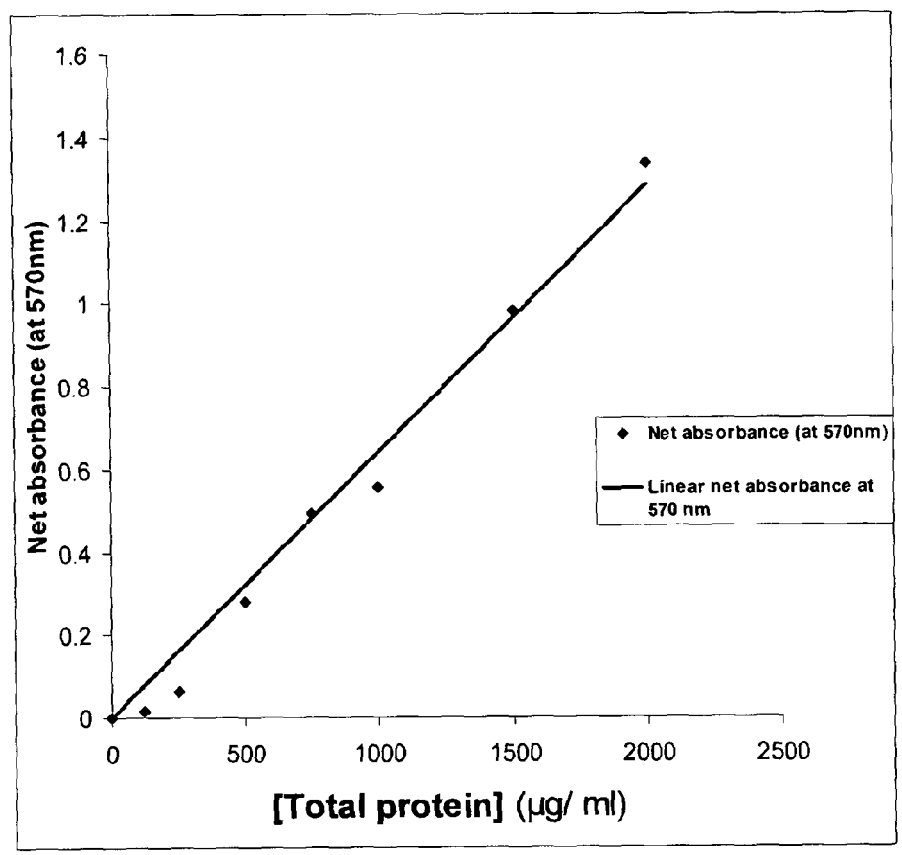

FIG. 18: Linear response for a dilution series of bovine serum albumin (BSA) sample.

Figure 19:
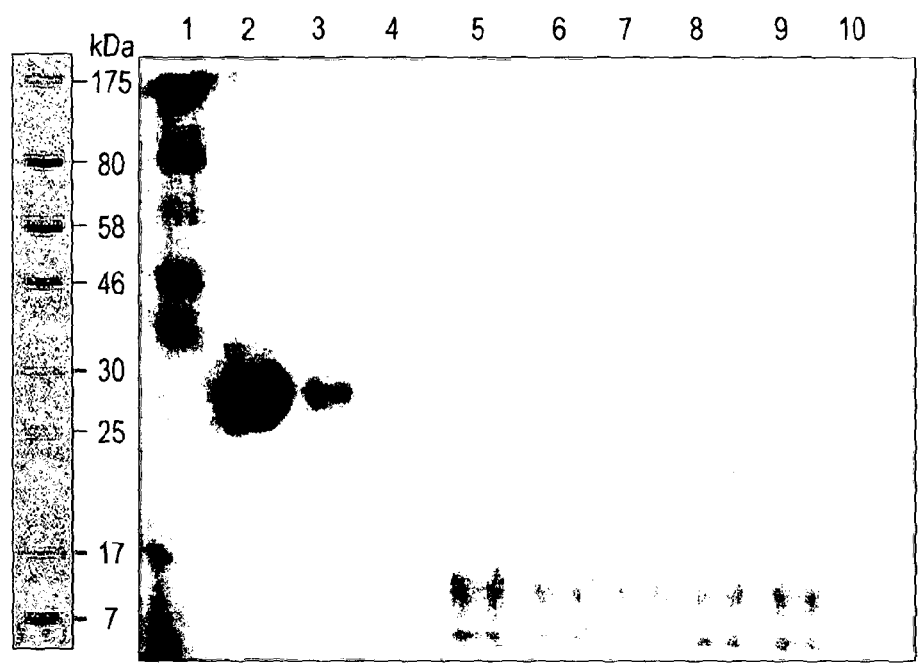

FIG. 19: SDS-PAGE gel showing the various periplasmic fractions of E. coli cells.

Figure 20:
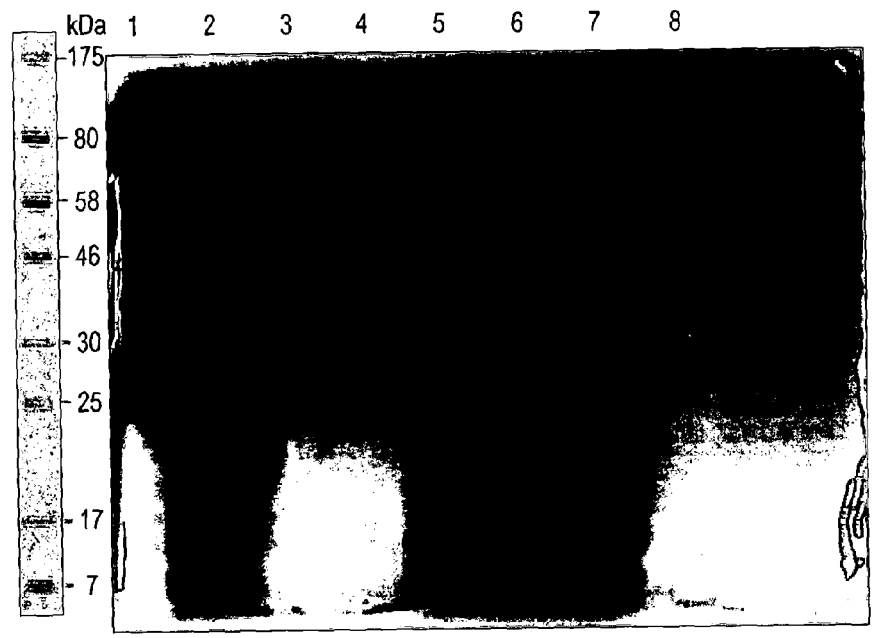

FIG. 20: SDS-PAGE gel showing the various periplasmic fractions of E. coli cells.

Figure 21:
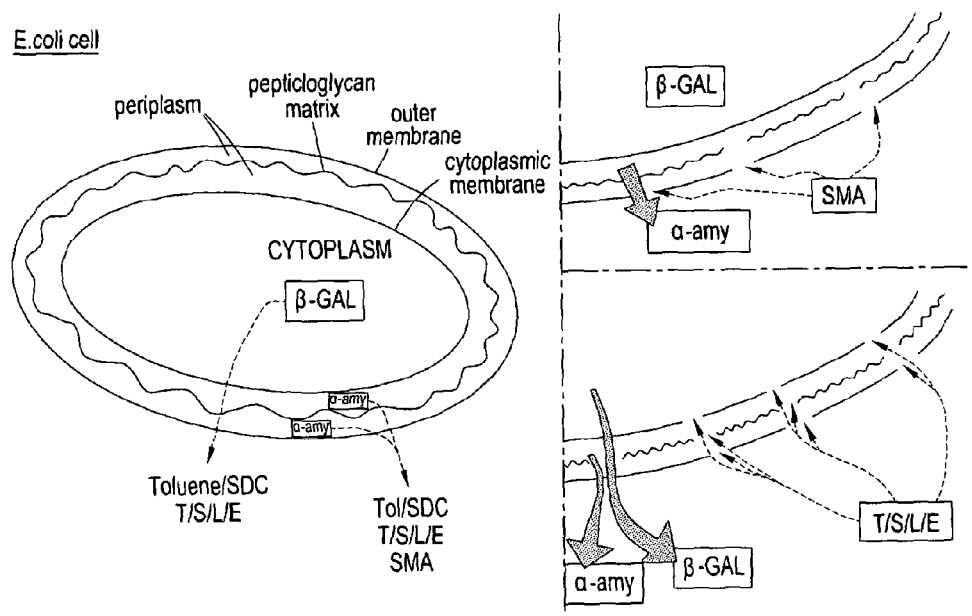

FIG. 21: Proposed mode of action of both TSLE and SMA on E. coli bacterial cells.

Figure 22:
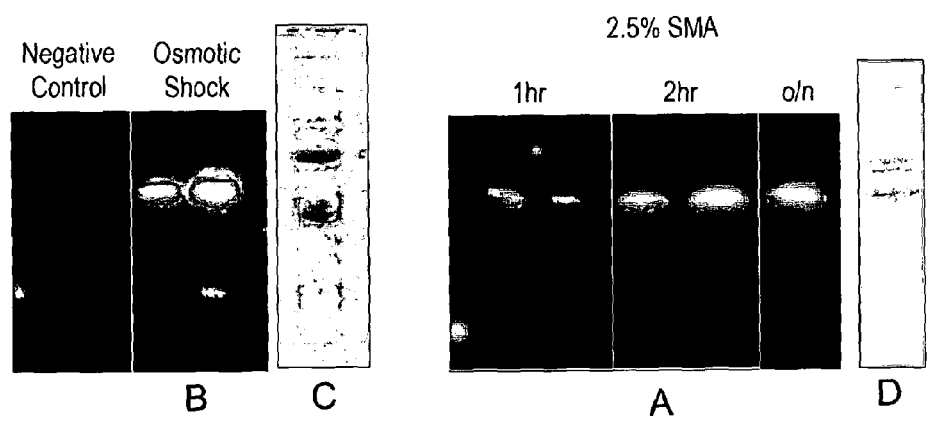

FIG. 22: The release of a FAB fragment from the periplasm of E. coli: (A) Western Blot results showing FAB fragment released from cells treated with SMA. (B) Western Blot results showing FAB fragment released from cells treated using osmotic shock. (C) SDS PAGE of total protein released from cells treated using osmotic shock. (D) SDS PAGE of total protein released from cells treated with SMA.

Example 1

Use of SMA to Selectively Release Protein from the Periplasm

Abstract

The recent discovery that the styrene maleic acid (SMA) copolymer can form lipid/polymer assemblies ('lipid nanodisks') in order to isolate and preserve transmembrane proteins has been a huge breakthrough in this field of biology. Therefore techniques including circular dichroism have been used to characterize these transmembrane proteins for structural and functional analysis (Knowles et al, 2009).

For several decades, there has been a need for an efficient, yet inexpensive treatment in order to selectively release proteins from the periplasmic space of *Escherichia coli* bacterial cells, that can be scaled up in a large bioprocessing industry (see FIG. 1 for a structure of the cell wall). During the present study, the inventors used the SMA copolymer as a method for releasing periplasmically based therapeutic proteins. This assay could be developed by investigating the impact of various factors on the efficiency of protein release; such as the varying of SMA concentration, differing incubation times, osmotic shock and the addition of EDTA. A positive control was used in all experiments—by comparing this new method with the optimal release method using Tris/Sucrose/Lysozyme/EDTA (TSLE). This new method of periplasmic protein release was developed using three biochemical assays (α-amylase, β-galactosidase and BCA total protein assays).

The inventors found out that the SMA copolymer can efficiently and selectively release proteins from the periplasm of *E. coli* cells. They found out that the ideal incubation conditions of these cells using this copolymer are at a concentration of 2-2.5% (at 37° C. for 2 hours). Therefore this new treatment has huge potential to be scaled up to a large-scale bioprocessing industry. This will significantly reduce the costs involved—due to SMA being relative inexpensive, and the need for fewer purification steps in downstream processing.

Introduction

The inventors decided to develop a new periplasmic protein release method in order to achieve a more efficient way of extracting periplasmically targeted therapeutic proteins. The most widely used method of periplasmic release uses the Tris/Sucrose/Lysozyme/EDTA (TSLE) buffer, and therefore was used as a control in the experiments. Using this TSLE release method, a high proportion of proteins can be released from the periplasm but this method is very hard to scale up for use in large-scale industrial processes, due to the amount and cost of the lysozyme enzyme.

Recently the discovery that a polymer named SMA (styrene maleic acid; FIG. 2) is able to bind to a lipid particle in order to form a SMA/lipid particle (SMALP) has been a huge breakthrough in the study of transmembrane proteins (Knowles et al, 2009; FIG. 3).

Hence the inventors decided to investigate whether the SMA copolymer can specifically disrupt the outer membrane of *E. coli* cells so as to selectively extract periplasmic proteins without the release of contaminant proteins from the cytoplasm.

Methods and Materials

BCA (Bicinchonic Acid) Assay to Determine the Total Protein Concentration

This assay is based on the colourimetic detection of a purple-coloured BCA-$Cu^+$ reaction complex (at 562 nm) to determine the total amount of protein in a sample. This protocol combines the reduction of copper ions ($Cu^{2+}$-->$Cu^+$) by a protein in an alkaline medium (termed the biuret reaction), with the ability of a single $Cu^+$ ion to be able to chelate with two molecules of BCA in order to form the purple-coloured reaction complex.

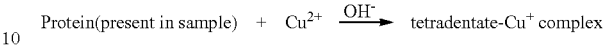

This reaction complex has a strong absorbance at 562 nm, which increases in a linear fashion over increasing concentrations of bovine serum albumin (BSA).

Preparation of 10% SMA 2000P

A solution of SMA 2000P (obtained from Sartomer) and 1M sodium hydroxide (10% w/v) was mixed gently overnight in a round bottom flask on a magnetic stirrer at room temperature (25 g of SMA 2000P dissolved in 250 ml of NaOH). A few anti-bumping granules were then added to the round bottom flask which was then placed on a heating mantle with a condenser attached. The SMA/NaOH solution was allowed to reach boiling point. After boiling, the heat was turned down and the solution was allowed to reflux for 2 hours, before being transferred to a cold room for 2 days. These processes were carried out in a fume cupboard. After this cooling period, the volume was measured and the percentage content of SMA was calculated, before being aliquotted into 50 ml falcon tubes and stored at −70° C.

Preparation of α-Amylase 126 Cultures.

The *E. coli* strain used was the K12 bacterial strain JM107 containing the plasmid pQR 126. Cells were grown overnight on nutrient agar plates containing 1% starch (w/v) and 20 μg/ml kanamycin. A single colony from this nutrient agar plate was inoculated into a conical flask containing 50 ml of 'Terrific Broth' (TB) supplemented with 20 μg/ml kanamycin, using aseptic technique, and inoculated overnight in a rotary shaker incubator at 37° C.

Cell Fractionation

This further overnight culture was divided into ten 40 ml aliquots in 50 ml Falcon tubes. These falcon tubes were subsequently centrifuged (3750 rpm) at 4° C. for 10 minutes using a Beckman-Coulter GS-6R centrifuge, before the supernatant (extracellular fraction) was discarded. The pellets were washed using 50 mM Tris buffer (pH 7.5) and re-centrifuged at 4° C. for 10 minutes (3750 rpm) before the supernatant was again removed.

Extraction of α-Amylase from the Periplasmic Fraction of *E. coli* Cells.

A single pellet of these cells was thoroughly re-suspended in 8 ml of Tris 50 mM (pH 7.5) and distributed into eight 1 ml aliquots in 1.5 ml Eppendorf tubes. These tubes were then centrifuged for 5 minutes at room temperature using a benchtop centrifuge (Spectrafuge™ 16M) at 14,000 rpm. The supernatant was then removed leaving a pellet. The periplasmic fractions were released from the *E. coli* cells using various extraction methods.

Lysozyme/EDTA Treatment

The traditional method of periplasmic release was achieved using lysozyme/EDTA. A single cell pellet was re-suspended in 1 ml of a buffer containing 50 mM Tris (pH 7.5), 20% sucrose, EDTA (1 mM) and lysozyme (500 μg/ml). This will subsequently be named as T/S/L/E buffer. This was then incubated for 15 minutes at room temperature, before the cells were collected by centrifugation for 5 minutes at room temperature at a speed of 14,000 rpm. The supernatant (periplasmic fraction) was decanted into a separate 1.5 ml Eppendorf tube.

In some experiments, a further 'cold water wash fraction' was obtained. This was achieved by washing the remaining cell pellet from the Eppendorf tube with 1 ml of ice cold deionized water (4° C.). The cells could then be collected by centrifugation for 5 minutes at room temperature (14,000 rpm) before the supernatant (cold water wash fraction) was decanted into a separate 1.5 ml Eppendorf tube.

Lysozyme Treatment

A single cell pellet was re-suspended in 1 ml of a buffer mixture containing 50 mM Tris (pH 7.5), 20° A) sucrose and lysozyme (500 μg/ml) before being agitated for 15 minutes at room temperature. The cells were then collected by centrifugation for 5 minutes at room temperature (14,000 rpm) before the supernatant (periplasmic fraction) was decanted into a separate 1.5 ml Eppendorf tube.

Tris/NaCl Treatment

A single cell pellet was re-suspended in 1 ml of a buffer containing 50 mM Tris (pH 8.0)/0.5 M NaCl before being incubated at 37° C., for a specific length of time (2 hours or 6 hours). After incubation, the cells were collected by centrifugation for 5 minutes at room temperature (14,000 rpm) before the supernatant (periplasmic fraction) was decanted into a separate 1.5 ml Eppendorf tube.

Styrene Maleic Acid (SMA) Treatment

Treatment by using various concentrations of styrene maleic acid (SMA) was also used to extract the periplasmic content of *E. coli* cells. A number of individual cell pellets were thoroughly re-suspended in a buffer containing differing concentrations of SMA (in 50 mM Tris pH 8.0/0.5 M NaCl) before being incubated either at room temperature or at 37° C., for varying lengths of time. After incubation, the cells were collected by centrifugation for 5 minutes at room temperature (14,000 rpm) before the supernatant (periplasmic fraction) was decanted into a separate 1.5 ml Eppendorf tube.

Lysozyme/EDTA or SMA Treatment Followed by an Osmotic Shock

Cells were thoroughly re-suspended in either 750 μl of T/S/L/E buffer (as described earlier) or 750 μl of SMA (in 50 mM Tris pH 8.0/0.5 M NaCl). The cell suspension was incubated statically for 15 minutes at room temperature, with either of these buffers. After this time an equal volume of cold water was added. This further cell suspension was incubated for a specific time period (depending on the specific condition) before recovery of the periplasmic fraction by centrifugation at 14,000 rpm for 5 minutes.

Preparation of Samples from α-Amylase Periplasmic Fractions for Analytical Ultracentrifugation (AUC)

The use of three separate α-amylase periplasmic fractions (TSLE, 2.5% SMA and 50 mM Tris/0.5 M NaCl) were required for use in AUC experiments. The T/S/L/E α-amylase fraction was dialyzed using a 12-14 kDa dialysis membrane. Whereas the SMA and Tris/NaCl α-amylase fractions were dialyzed using a 3.5 kDa dialysis membrane. All of these fractions were dialyzed in a buffer containing 50 mM Tris pH 8.0/500 mM NaCl in order to obtain highly pure samples without the presence of contaminants. Analysis of these samples was subsequently performed using analytical ultracentrifugation.

Assay to Determine the Amount of α-Amylase Released by the Periplamic Space of Bacterial Cells.

The stop solution required for use in the assay was made up using 100 μl of iodine stock solution (2.2% $I_2$/4.4% KI) dissolved in 50 ml potassium iodide (2% w/v).

The activity of the α-amylase enzyme was determined by using an assay in which enzyme activity is calculated by measuring the decrease in the rate of absorbance of a starch/iodine complex (2.2% $I_2$/4.4% KI).

Dilutions of the periplasmic fractions were prepared in a 1:10 ratio (100 μl sample plus 900 μl Tris 200 mM pH 7.5), and 150 μl of each diluted periplasmic fraction was placed in a separate well of a 96-well plate and pre-incubated at 50° C. At the start of the assay, 150 μl of a pre-incubated (50° C.) starch solution (0.5% w/v) was added to the appropriate wells using a multi-channel pipette at staggered time intervals. This reaction was allowed to occur for 3 minutes at 50° C.

After 3 minutes, 15 μl of each reaction mixture was added into appropriate wells on a different 96-well plate, containing 300 μl of stop solution ($I_2$/KI). After addition of the reaction mixture for each periplasmic fraction, the absorbance was measured on a Molecular Devices™ E-max Precision plate reader at 590 nm. Each of these reactions was carried out in either duplicate or triplicate for each fraction in order to obtain multiple data sets.

The efficiency of α-amylase activity was then able to be calculated by measuring the decrease in the absorbance rate of a starch/iodine complex.

SDS-PAGE of the Periplasmic Fractions

The periplasmic fractions (20 μl) were combined with 5 μl of protein sample loading dye before being loaded into wells on the SDS-PAGE gel. The gel was run at 100 V for about one hour, until the protein marker had reached the end of the gel. The gel was subsequently stained using Instant Blue™ (Coomassie Blue) and placed on a rocker until a number of protein bands became visible. After this staining process, the Instant Blue™ stain was removed and the gel was destained overnight by using deionized water. The protein bands present on the gel were then analyzed against the pre-stained protein marker in order to determine the sizes of the proteins present.

Growth of Cultures for β-Galactosidase Measurements

The *E. coli* strain used in this assay was the M182 bacterial strain MALX 400 containing the plasmid pACYC ΔHN. These cells were grown overnight on nutrient agar plates containing tetracycline and chloramphenicol.

A single colony from this nutrient agar plate was inoculated using a sterile loop into a flask containing 10 ml LB supplemented with 10 μg/ml chloramphenicol and 35 μg/ml tetracycline, using aseptic technique, and incubated overnight in a shaking water bath at 37° C. After incubation, another conical flask containing 10 ml LB (with tetracycline and chloramphenicol) was inoculated with 200 μl of the overnight preculture and shaken in a 37° C. water bath for 2-3 hours. This was done until the optical density at 650 nm ($OD_{650\,nm}$) was between 0.3 to 0.5, at which time the culture was stored on ice.

To permeabilize the cells, 50 μl of both toluene and 1% sodium deoxycholate were added to the culture and mixed briefly by covering the neck of the flask with parafilm. The culture was then aerated at 37° C. in a shaking water bath in order to evapoarate the toluene. The lysates were stored in an ice bucket until required for experimental use.

Preparation of Z-Buffer, ONPG and $Na_2CO_3$ for Use in β-Gal Assays

The Z-buffer for use in the β-galactosidase assay was made up using 0.06 M $Na_2HPO_4$, 0.04 M $NaH_2PO_4$, 0.01M potassium chloride (KCl), 0.01 M $MgSO_4$ and 0.05 M β-mercaptoethanol (which was added on the day of the experiment).

The ONPG solution was required to be made up to a concentration of 4 mg/ml. This was achieved by adding 80 mg of freeze-dried ONPG powder into 20 ml of Z-buffer. A sodium carbonate ('stop reagent') was also required to be made up to a final concentration of 1 M.

The Z-buffer (1.9 ml) was measured into the required number of test tubes, including test tubes for the control experiments. Aliquots of the cell lysate (100 μl) were added to the tubes for the β-galactosidase measurements, whereas 100 μl of Z-buffer was added to the control tubes.

β-Gal Tubes:
1.9 ml Z-buffer+0.1 ml cell lysate→.5 ml ONPG→1 ml $Na_2CO_3$

Control I (no cell lysate):
−2 ml Z-buffer→0.5 ml ONPG→1 ml $Na_2CO_3$

Control ii (absence of ONPG):
−1.9 ml Z-buffer+0.1 ml cell lysate→0.5 ml Z-buffer→1 ml $Na_2CO_3$.

The reaction was started by adding 0.5 ml o-nitrophenyl-β-D-galactoside (ONPG) and allowed to occur for 0, 5, 10 and 20 minutes respectively. After these specific times, the reaction was stopped using 1 ml of 1 M $Na_2CO_3$ before recording the optical density at 420 nm ($OD_{420nm}$). For the tubes testing β-gal activity at 0 minutes, the sodium carbonate was added before the ONPG. The β-galactosidase activity for each of the test tubes, was then calculated for the cultures at the appropriate times.

During these test tube assays, the absorbance was measured using a Cecil Instruments™ CE-272 Linear Readout Ultraviolet Spectrophotometer Adaptation of β-Gal Assay in Order to Fit in a 96-Well Plate The same basic protocol was followed for another set of experiments, but the volumes of solutions were scaled down by ten-fold in order to fit the reaction mixture into a 96-well plate. So for the samples, 190 μl of Z-buffer was added into the specific wells in the plate—with the addition of 10 μl of β-galactosidase containing cells or cellular fractions For the reaction to begin, 50 μl of ONPG (o-nitrophenyl-β-D-galactoside) was added to the specific wells, and the reaction was allowed to occur for 0, 5 and 20 minutes. The reaction was stopped by adding 100 μl of 1 M sodium carbonate ($Na_2CO_3$) solution, and the optical density at 450 nm was measured ($OD_{450}$) using a plate reader.

During this set of experiments a number of control tests were carried out. A positive and negative control was carried out using an Eppendorf tube containing 1 ml of β-galactosidase cells which had been permeabilized using 5 μl toluene and 5 μl sodium deoxycholate (with or without the addition of ONPG). Whereas another negative control test was carried out, without the use of the cell lysate/fraction altogether. Cell fractions containing the enzyme of interest (β-galactosidase) were extracted using the same method as described for the α-amylase assay (described earlier).

Bicinchonic Acid (BCA) Assay Carried Out in a 96-Well Plate to Detect the Amount of Total Protein The BCA working reagent is prepared by mixing 50 parts of BCA Reagent A, with 1 part of BCA reagent B. In the case of this assay, 9.8 ml of Reagent A is mixed with 0.2 ml of Reagent B. This working reagent can then be stored at room temperature and is stable for a day.

Using a 96-well microassay plate, 10 μl of each standard or sample (periplasmic fraction) was added to appropriate wells in the plate. To this volume of standard or sample, 200 μl of working reagent was added. A set of blank solutions were also made up in the appropriate wells in a plate using 10 μl of the appropriate buffer, made up with 200 μl of working reagent. The plate was mixed on a rocker for 30 seconds, before being incubated at 37° C. for 30 minutes. The absorbance was then measured using a plate reader at 570 nm. The average absorbance for the blanks at 570 nm was then subtracted from the average absorbance for each of each standard or unknown sample, in order to create a BSA standard curve. From this BSA standard curve, the protein concentrations of each particular periplasmic fraction could be determined.

Results

The Effect of Varying Conditions Upon Periplasmic α-Amylase Release from *Escherichia coli* Cells.

In order to extract α-amylase from the periplasm of *E. coli* cells (K12 bacterial strain JM107 containing the plasmid pQR 126) an initial α-amylase assay was set up to investigate the effect of varying conditions on the release of this enzyme.

In this initial assay, individual α-amylase pellets were treated with a number of buffers in order to extract the periplasmic contents of *E. coli*. These different periplasmic release methods included using Tris/Sucrose/Lysozyme (TSL) buffer, Tris/Sucrose/Lysozyme/EDTA (TSLE) buffer, 2.5% Styrene Maleic Acid (SMA) polymer buffer (under various temperatures and incubation times) and Tris/NaCl buffer.

As predicted the treatment of the α-amylase 126 pellet with a TSLE buffer gave the highest extraction of α-amylase (80.5%), but there were some promising results when other individual α-amylase 126 pellets were treated with the styrene maleic acid polymer (at 2.5% concentration). Also the TSLE buffer gives a 35% greater release of α-amylase from *E. coli* cells compared to the TSL periplasmic release method (80.5% compared to 45.7%). This therefore indicates that EDTA has a stimulatory effect on the mode of action of lysozyme.

The most striking of these conditions for periplasmic protein release was when α-amylase 126 cells were treated with 2.5% SMA polymer for 2 hours at 37° C., which gave a 68% extraction of this enzyme (FIG. 4). Therefore compared to the optimal release method using TSLE (100%), this SMA periplasmic release method was 84.5% efficient (FIG. 5). After these initial results there was a need to try and develop an improved assay to test the effect of varying conditions upon the SMA treatment of these *E. coli* cells.

Explanation of Error Bars for α-Amylase Assay Graphs

For each of these assays carried out during this research, the reactions were carried out in duplicate or triplicate in order to obtain multiple data sets. Therefore the graphical bar columns represent the average percentage (%) of α-amylase extracted from the periplasm for each periplasmic protein release method.

Due to these multiple data sets there is a need to include error bars in each graph. Therefore for each graphical bar column the upper error bar represents the maximum extraction of α-amylase from the periplasm, whereas the lower error bar represents the minimum extraction of α-amylase from the periplasm for each periplasmic protein release method.

Periplasmic α-Amylase Extraction Increases Over an Increased Incubation Period at 37° C.

After this initial result, there was a need to develop an α-amylase assay in order to show the temporal effect of a 37° C. incubation upon the periplasmic extraction of α-amylase by the SMA copolymer. In separate assays, these *E. coli* cells were therefore exposed to a wide range of different incubation times at 37° C.

The results for the first of these assays (FIG. 6) showed a hugely significant temporal increase (~5 fold) in the amount of α-amylase extracted from the periplasm of these cells between 15 minutes (13.8%) and 2 hours (67.2%). This result indicates that giving the SMA lipid polymer longer to function must increase the probability of extracting α-amylase from the periplasm of *E. coli* bacterial cells.

There was a need to develop this assay further to test the effects of longer incubation times (at 37° C.) with SMA (between 2 hours and 6 hours), on periplasmic α-amylase extraction from *E. coli* bacterial cells. The results for this assay (FIG. 7) showed only a negligible increase in the release of this enzyme (78.7% to 82.3%) between these time periods.

There was a need to combine the results from these two separate time-course assays in order to measure the efficiency of the various periplasmic protein release methods (FIG. 8). Therefore these results showed that the incubation of these *E. coli* cells with 2.5% SMA for 2 hours (at 37° C.) gave the most promising result, giving a periplasmic release of α-amylase which was 90.9% efficient compared to the optimal TSLE release method (100%).

Periplasmic α-Amylase Extraction Decreases as the Concentration of Styrene Maleic Acid (SMA) is Increased There was a need to further develop this assay in order to test the effects of different concentrations of SMA (between 0.5% and 4.5%) on the extraction of α-amylase from the periplasm of *E. coli* cells. In order to maintain a constant, the incubation time was kept at 2 hours (at 37° C.) for each of these SMA concentrations.

A number of separate assays were set up with different concentrations of SMA. The first of these α-amylase assays (FIG. 9) showed a significant decrease in the extraction of periplasmic α-amylase (64.3% to 29.3%) between 2% and 4.5% SMA. This assay was further developed to investigate the extraction of α-amylase from the periplasm of *E. coli* cells, when treated with SMA concentrations between 0.5% and 2.5%. The results for this assay (FIG. 10) showed that there was a marked increase (59.7% to 81.6%) in the amount of α-amylase extracted from these *E. coli* cells.

There was a need to combine the results from these two separate assays to measure the efficiency of these various periplasmic release methods (FIG. 11). When this was done both 2% and 2.5% SMA gave almost identical results compared to the optimal release method (TSLE buffer) in terms of the release of α-amylase from the periplasm. This result indicated that the SMA lipid polymer gave a very good release of α-amylase from the periplasm.

Temperature has No Effect on the ISLE Method of Periplasmic α-Amylase Release

A new assay was set up to investigate the effects of temperature on the TSLE treatment of *E. coli* cells. The optimal TSLE release method (incubation at room temperature for 15 minutes) was compared to a similar length incubation of a separate pellet of α-amylase 126 cells, at 4° C. (FIG. 12). When these two temperatures were compared in terms of their respective releases of α-amylase, there was no realistic difference (100% to 99.5%).

The Effect of a 'Cold Water Wash' on Periplasmic Protein Release

A 'cold water wash fraction' was obtained (described previously in methods) when washing a previous pellet with ice cold water. The results obtained from these fractions showed there was a significant decrease in α-amylase release compared to the optimal TSLE periplasmic release method (FIG. 12), giving either a 17.3% release (at room temperature) or 5.4% (at 4° C.) release of α-amylase. This result indicated that most of the α-amylase produced from these conditions was released in the 'periplasmic fraction'.

The Effect of an Osmotic Shock on the Efficiency of Periplasmic α-Amylase Release A further assay was carried out in order to test the effect of an addition of an appropriate volume of ice cold water on the extraction of α-amylase from the periplasm of *E. coli* cells. For this assay this osmotic shock procedure (see methods) was carried out in conjunction with the TSLE, 2% SMA and 2.5% SMA treatments for periplasmic protein release (FIG. 13). The results for this assay showed that an osmotic shock had little to no effect on the efficiency of the T/S/L/E treatment to release α-amylase from the cells (100% to 99.3% efficiency). But there was a slight increase in the amount of α-amylase released when an osmotic shock was used in conjunction with both the SMA treatments; 2% (85.9% to 92.6%) and 2.5% SMA. (75.8% to 88.4%).

The Effect of EDTA on Various Periplasmic Protein Release Methods

The effect of EDTA on lysozyme action has already been shown previously (FIG. 4) and was found to have a stimulatory effect on the amount of α-amylase released from the periplasm of *E. coli* cells. Therefore there was a need to see if EDTA had any effect on the ability of SMA lipid particles (SMALPs) to release α-amylase from the periplasmic space of *E. coli*.

When the same concentration of EDTA (1 mM) was added to a 2% SMA buffer using a varying set of incubation conditions, there was shown to be a significant decrease in the amount of α-amylase released from the periplasm of these *E. coli* cells. For example, when the periplasmic α-amylase release from *E. coli* cells was investigated using the 2% SMA buffer at 37° C. for 2 hours (with and without the addition of EDTA), there was a significant decrease in the amount of α-amylase released from the periplasmic space (FIG. 19). The amount of α-amylase decreased from 79.5% to 4.2%, compared to the TSLE optimal release method (100%).

The Effect of Varying Conditions on the Release of β-Galactosidase from *E. coli* Cells.

An initial test tube assay was set up to show the presence of β-galactosidase in these *E. coli* cells. This was achieved by permeabilizing the cells using toluene and sodium deoxycholate. In the presence of ONPG, over a 20 minute time period (at an optical density of 420 nm) there was a change in absorbance of 0.53 (from 0.05 to 0.58), therefore indicating a significant release of 3-galactosidase. Whereas in the absence of ONPG, over a similar time period (at the same optical density), there was no change in absorbance. In this case, the β-galactosidase released cannot exert its action because ONPG (colourless) cannot be converted to ONP (yellow). In another negative control experiment, with Z-buffer in the presence of ONPG, there was also no change in absorbance (at 420 nm). This is because there are no cells present containing this enzyme. For each of these β-galactosidase assays, the change in absorbance represented the increased activity of this enzyme (FIG. 15).

To investigate the effect of different treatments and conditions on the release of the cytoplasmic enzyme β-galactosidase from *Escherichia coli* cells (M182 bacterial strain MALX 400 containing the plasmid pACYC ΔHN), several different assays were set up in 96-well plates.

In the first of these assays the cells were treated with TSLE buffer, 2% SMA buffer and 2.5% SMA buffer (FIG. 16). Also the cells could be permeabilized with toluene and sodium deoxycholate in order to release β-galactosidase as a positive control. The results of this assay showed positive results (β-galactosidase release) for the TSLE treatment as well as for the permeabilized cells (in the presence of ONPG). Whereas the release of β-galactosidase was either none or minimal when the cells were treated with the SMA polymer. A negative control experiment was carried out with the presence of β-galactosidase (permeabilized cells) with the absence of ONPG. Therefore in the absence of this β-gal substrate, there was no change in absorbance (at 450 nm) detected.

These results showed that the TSLE treatment was able to extract β-galactosidase from the cytoplasm of *E. coli* cells whereas the negative result shown by the SMA treatment release indicated that the SMA lipid particles (SMALPs) don't release any of this cytoplasmic enzyme.

In a subsequent assay in order to detect the release of β-galactosidase, a Tris/NaCl buffer was used to release the periplasmic contents of *Escherichia coli* cells (FIG. 17). This specific buffer again led to no release of β-galactosidase, which once again indicated that the cytoplasmic membrane must remain intact.

The Effect of a 'Cold Water Wash' on the Release of β-Galactosidase

The procedure of obtaining a 'cold water wash fraction' from β-galactosidase cells (method described previously) was used in order to detect the release of this enzyme. The results from this treatment showed that no β-galactosidase was released in the 'cold water wash fraction' (cwf). This indicated that all the β-gal was released in the 'periplasmic fraction' (FIG. 17).

The Use of a Bicinchonic Acid (BCA) Assay in Order to Detect the Amount of Total Protein Present in Periplasmic and Cold Water Wash Fractions This assay was used to detect the amount and concentration of protein present in a number of periplasmic fractions (pf's) and cold water wash fractions (cwf's) extracted from *E. coli* cells. The net absorbance of each of these fractions was plotted on a BSA standard curve in order to determine the total protein concentration (FIG. 18).

The highest amount of total protein detected from the periplasmic fractions of *E. coli* cells (K12 bacterial strain JM107 containing the plasmid pQR 126) was by using the optimal TSLE method of periplasmic protein release, which gave a net absorbance of 0.3625 (at 570 nm) therefore indicating a total protein concentration of ~500 μg/ml. This result indicated that the TSLE buffer is able to break down the outer and cytoplasmic membranes in order to release a greater amount of proteins from both the periplasmic space and the cytoplasm.

When the cells were treated with 2.5% SMA [in 50 mM Tris (pH 8.0)/0.5 M NaCl] in order to release the periplasmic contents, there was a smaller net absorbance of 0.112 which indicated that a smaller amount of total protein is being released from the cell (~200 μg/ml). This is again indicative of previous results, because protein is only being released from the periplasm and not the cytoplasm of these *E. coli* cells. Also, when the cells were treated with the Tris/NaCl buffer in order to release the periplasmic contents there was a lower net absorbance of 0.0615 (~100 μg/ml). This result indicated that less protein was released using this method, which again is indicative of previous results displayed from α-amylase assays. Using the 'cold water wash fractions' from these methods gave no real change in the net absorbance at 570 nm. This showed that very little or no protein was released using this method.

The results from this specific BCA total protein assay were very similar for the periplasmic fractions obtained from the β-galactosidase *E. coli* cells (M182 bacterial strain MALX 400 containing the plasmid pACYC ΔHN). The only difference was from using the optimal TSLE release method, which gave a slightly lower net absorbance of 0.254, indicating a total protein concentration of ~400 μg/ml.

This indicated that slightly less protein was released from these *E. coli* cells using the optimal TSLE periplasmic protein release method—due to the fact that less α-amylase is present in these cells compared to the other bacterial strain. The line of best fit indicates the linear net absorbance of a known standard or protein sample at 570 nm (with an intercept at 0 on the x- and y-axes).

An SDS-PAGE gel was run to show the presence of various proteins in the periplasmic fractions of *E. coli* cells. The results are shown in FIG. 19.

Separate bands were present in lanes 2 and 3 at around the same molecular weight (in kDa). The band is more pronounced in lane 2 as this is the TSLE buffer alone, whereas the band in lane 3 represents the TSLE periplasmic fraction. This band most probably represents the lysozyme present either in the buffer or periplasmic fraction. The SMA polymer was indicated in lanes 5-9 due to the use of a 2.5% SMA periplasmic release treatments. This is indicative of a band representing a smaller protein of around 7.5 kDa. All the periplasmic fractions used for this SDS-PAGE gel were also used in the α-amylase assay and were run against a pre-stained protein marker (Lane 1).

There was a need to run a further SDS-PAGE gel in order to investigate the proteins used in the extraction of the periplasmic contents of *E. coli* cells (FIG. 20).

There is a protein band present in lane 1 (TSLE periplasmic fraction) of the gel, which most probably represents the lysozyme protein. This is in contrast to lane 2 (2.5% SMA periplasmic fraction) of the gel which shows a band representing a smaller protein (SMA lipid polymer) of around 7.5 kDa.

A similarly sized band to lane 2 is found in lanes 5 to 7. These lanes represent the dimyristoyl phosphatidylcholine (DMPC) disks, phosphatidylcholine (PC) disks and the 2.5% SMA buffer respectively.

In lane 4 of the gel the α-amylase protein was run by itself. This is indicative of a band representing a larger protein (~54 kDa). These periplasmic fractions/proteins were run against a pre-stained protein marker (lane 8).

Basic Results Guideline to Project in Terms of the Amounts of Different Proteins Released From *E. coli* Cells Using these Three Biochemical Assay Methods

|  | A-amylase release | β-galactosidase release | Total protein release |
|---|---|---|---|
| TSLE pf | + + + + + (100%) | + + + + + | + + + + + (~500 μg/ml) |
| TSLE cwf | + (5.4%-17.3%) | − | − |
| Styrene maleic acid (SMA) lipid polymer | + + + + (+) (~80-99.4%) | − | + + (~200 μg/ml) |

NOTE:
Throughout the project the SMA periplasmic protein release treatment gave a α-amylase release which varied from ~80-99.4% compared to the optimal TSLE method. This difference is only due to the use of this treatment in a number of separate assays.
Key
(−) = indicates no release of that particular protein
(+) OR (+ +) = indicates minimal release of that particular protein
(+ + + +) = indicates a very good release of that particular protein
(+ + + + +) = indicates an excellent release of that particular protein Discussion The recent study by Knowles et al has opened up a whole new way of studying transmembrane proteins. This is due to the formation of 'monodispersed lipid disks by the styrene maleic acid (SMA) copolymer'. The formation of these lipid 'nanodisks' (SMALPs) can lead to transmembrane proteins being preserved in order to be accurately studied for biophysical and structural analysis, such as nuclear magnetic resonance (NMR) spectroscopy and circular dichroism (CD) spectroscopy.

This discovery that SMALPs can bind to and form a complex with the outer membrane has led to the theory that these lipid nanodisks can be used as a possible means to isolate and extract proteins from various other membrane compartments (I.e. periplasm).

To date the optimal method of protein extraction from Gram-negative bacteria (i.e. *E. coli*) in terms of the greatest amount of protein released uses the lysozyme enzyme in conjunction with EDTA.

Lysozyme is known to target the peptidoglycan component of the cell wall of bacteria. Therefore in Gram-positive bacteria (i.e. *Bacillus* species), lysozyme can easily breakdown this layer. In Gram-negative bacteria, such as *E. coli*, the presence of an additional outer membrane can protect the peptidoglycan layer from the outer environment. The addition of agents, such as EDTA, can lead to the chelation of divalent cations ($Ca^{2+}$, $Mg^{2+}$) causing the destabilization of the outer membrane—therefore allowing lysozyme to access the peptidoglycan layer present in the periplasmic space, and subsequently leading to a high amount of protein being released from the 'lysed' cell.

The periplasmic protein release of *E. coli* bacterial cells by lysozyme/EDTA treatment is also not dependent on temperature, as this factor leads to no significant change in the release of proteins from the periplasmic space.

The treatment of *E. coli* cells with the SMA copolymer at a concentration of 2.5%, for 2 hours at 37° C. gave a promising result—in terms of the release of proteins from the periplasm (FIG. 1). Due to the presence of phospholipids, lipopolysaccharides and lipoproteins in the outer membrane of *E. coli* cells, these specific SMA polymers are able to form polymer/lipid assemblies—otherwise known as 'lipid-nanodisks' (Knowles et al, 2009). The formation of these complexes can lead to the release of proteins from the periplasm. The ability of the SMA copolymer to form lipid/polymer assemblies in order to release periplasmic proteins was tested under a variety of conditions—such as differences in concentration of the polymer (FIGS. 6-8), temperature, and the time course of the assay.

Using the 2.5% SMA polymer at 37° C. to treat *E. coli* cells—for times ranging from 15 minutes to 6 hours led to a hugely significant increase in the release of α-amylase from the periplasm. As the SMA lipid polymer (SMALP) interacts with the outer membrane over a period of time this leads to the release of a greater amount of periplasmic α-amylase. This reaction seems to be pretty much exhausted at 2 hours, as only a very little amount of α-amylase is released thereafter.

Therefore the treatment of *E. coli* cells with the SMA copolymer for 6 hours would not be a viable option in the bioprocessing industry, due to increased costs of running the incubator at 37° C., so the 2 hour treatment with 2.5% SMA is likely to be more economical in terms of a bioprocess design to release periplasmically targeted therapeutics.

Using the SMA polymer at various concentrations, from 0.5% to 4.5% (at 37° C. for 2 hours), gave different results in relation to the amount of α-amylase released from the periplasm of *E. coli* cells. This result indicated that as the concentration of SMA increased (between 2.5% to 4.5%), this would have an inhibitory effect on the ability of the SMA to form lipid/polymer assemblies to release the contents of the periplasm of *E. coli* cells. Another possibility could be that as the concentration of SMA increases up to 4.5° A), this may lead to the native unfolding of periplasmic α-amylase, which needs to confirmed by circular dichroism analyses. Therefore the periplasmic environment may become less oxidative—so that the protein cannot form its characteristic tertiary structure. Whereas when the concentration of SMA increased (between 0.5% to 2.5%) this gave an increased release of periplasmic α-amylase, which suggested that the lipid/polymer assembly complex is able to bind at an increased strength to the outer membrane—stimulating an increased release of α-amylase. Therefore using styrene maleic acid (at 2-2.5%) is likely to be the best option for use in bioprocessing as a more economical option of obtaining proteins from the periplasm of *E. coli* cells.

Also when the SMA copolymer (at 2% concentration) was used in conjunction with 1 mM EDTA this led to a minimal release of α-amylase from the periplasm. This could indicate that EDTA disrupts the SMA lipid particles (SMALPs) from forming on the outer membrane of *E. coli*. The failure of the lipid/polymer assemblies to form therefore results in very little or no periplasmic protein release.

During this study, an osmotic shock (developed from French et al, 1996) was used in conjunction with various periplasmic release treatments. The addition of water had a slightly positive effect on the SMA method of releasing α-amylase. This could indicate the increased or tighter assembly of the SMALP complex at the outer membrane via an osmotic shock could lead to a more stable periplasmic protein release mechanism.

During bioprocessing methods, if targeting periplasmically based therapeutic proteins, there is a need to selectively remove proteins from the periplasm—without releasing contaminants from the cytoplasm. The release of a cytoplasmic enzyme, β-galactosidase, was tested in a new assay using the same protein release methods. The results achieved were very interesting in the fact that the TSLE treatment released a large proportion of β-galactosidase, whereas the SMA (at 2 and 2.5% concentration) treatment didn't release any of this enzyme. This suggests that the SMA polymer only forms a complex at the outer membrane and doesn't target the inner cytoplasmic membrane. The formation of 'lipid nanodisks' at the outer membrane could also be due to the strong negative charge exhibited by this membrane. This negative charge is due to the presence of lipopolysaccharides and lipoproteins.

Therefore combining results from earlier assays with this striking result; the SMA treatment is able to give a very high release of α-amylase from the periplasm without contamination from any cytoplasmic proteins. This could be very important in the bioprocessing industry, as the release of a pure protein in the initial 'cell disruption' step could drastically reduce the further costs involved in downstream processing (Bracewell et al, 2009) in the production of periplasmically based therapeutics (biopharmaceuticals).

The high release of β-galactosidase by the TSLE treatment of *E. coli* cells is due to the fact that lysozyme acts as a murimidase in order to break down specific linkages in the peptidoglycan layer. Previous studies (Vollmer et al, 2004; Demchick and Koch, 1996) have shown that the peptidoglycan layer contains pores with a mean radius of 2.06 nm. Therefore pores of this size should be able to allow the penetration of a globular protein with a mass of 22-24 kDa. Therefore, lysozyme (with a molecular weight of 14-15 kDa) will easily be able to pass through these pores in order to damage the cytoplasmic membrane. Also electron microscopy studies of negatively stained SMALPs (Knowles et al, 2009) have indicated an average diameter of ~11 nm of these complex lipid/polymer assemblies. Therefore these SMALPs are unable to pass through the pores present in the peptidoglycan layer—so they can selectively target the release of periplasmic proteins.

The minimal or absence of release of both α-amylase and β-galactosidase using the ISLE 'coldwater wash fractions' is an indication of the very high amount of these proteins present in the initial periplasmic fraction. Therefore indicating the increased efficiency of this method in releasing the maximum amount of protein in this first periplasmic fraction.

The results achieved from both the α-amylase and β-galactosidase biochemical assays were confirmed by the use of a BCA total protein assay. The higher amount of total protein released from *E. coli* cells by the TSLE periplasmic protein release method was representative of the release of high amounts of both α-amylase (from the periplasm) and β-galactosidase (from the cytoplasm). Whereas the reduced amount of total protein released from the *E. coli* cells by the SMA periplasmic protein release method is representative of earlier results displaying a very high α-amylase release, with no contamination from cytoplasmic proteins.

Conclusions

In conclusion, even though the TSLE protein release method may sometimes give a slightly higher amount of α-amylase, this can be contaminated by the release of cytoplasmic proteins (I.e. β-galactosidase)—therefore in a large-scale bioprocessing industry this would be a costly option, due to the cost of using the lysozyme and also in subsequent purification steps in downstream processing. Whereas, the use of styrene maleic acid (SMA) can be used to selectively release proteins from the periplasmic space (FIG. 21) by forming a SMALP complex at the outer membrane. Therefore in a large-scale bioprocessing industry this method would be of better economical value due to the reduced costs of the styrene maleic acid polymer and the fact that fewer purification steps would be needed to produce this protein.

REFERENCES

French C., Keshavarz-Moore E., Ward JM.—'Development of a simple method for the recovery of recombinant proteins from the *Escherichia coli* periplasm'—*Enzy. Micro. Tech.* 1996; 19; 332-338.
Knowles T J, Finka R, Smith C, Lin Y P, Dafforn T, Overduin M.—'Membrane proteins solubilized intact in lipid containing nanoparticles bounded by styrene maleic acid copolymer'—*J Am Chem. Soc.* 2009 Jun. 10; 131 (22):7484-5.
Vollmer W., Holtje J V. (2004)—'The Architecture of the Murein (Peptidoglycan) in Gram-Negative Bacteria: Vertical Scaffold or Horizontal Layer(s)?'—*J. Bacteriol.* 186 (18); 5978-5987
Demchick, P., and A. L. Koch.—'The permeability of the wall fabric of *Escherichia coli* and *Bacillus subtilis.*'—*J. Bacteriol.* 178:768-773.

Example 2

Release of FAB Antibody Fragments from the Periplasm of *E. Coli* Using SMA

*E. coli* were transformed with a plasmid containing a gene coding for an antibody fragment (FAB fragment) fused to a periplasmic export sequence. Cells were grown and the expression of the gene induced. Cells were separated by centrifugation and then re-suspended in buffer solution (e.g. 50 mMTrisHCl pH 7.4, 150 mMNaCl) containing increasing amounts of SMA at 37° C. After incubation for 1 hour spheroplasts were separated from solution by centrifugation and the supernatant (containing the FAB fragments) was collected. The amount of FAB fragment released was assessed using a Western blot probed with an antibody for the FAB fragment. The total protein in the supernatant was assessed using SDS PAGE.

As shown in FIG. 22, the amount of FAB fragment released when cells expressing the FAB fragment are treated with 2.5% SMA at 37° C. for 2 hours (A) is equivalent to that obtained using existing osmotic shock methods (B). The amount of non-FAB fragment protein released using the SMA method (D) is significantly lower than using osmotic shock (C).

The invention claimed is:

1. A method for releasing the content of the periplasmic space of bacterial cells comprising incubating the bacterial cells in a solution containing styrene maleic acid copolymer (SMA) so as to specifically disrupt the outer membrane of the bacterial cells in order to release the content of the periplasmic space without disrupting the inner membrane, such that the content of the periplasmic space is released, wherein the method comprises a further step of separating spheroplasts from the solution.

2. The method of claim 1, wherein the styrene: maleic acid ratio is between 1:2 and 10:1.

3. The method of claim 1, wherein the styrene: maleic acid ratio is approximately 2:1.

4. The method of claim 1, wherein the SMA is at a concentration of between 0.5-4.5%.

5. The method of claim 4, wherein the SMA concentration is approximately 2-2.5%.

6. The method of claim 1, wherein the bacterial cells are incubated with the SMA for between 15 minutes to 6 hours.

7. The method of claim 6, wherein the bacterial cells are incubated with the SMA for approximately 2 hours.

8. The method of claim 1, wherein the bacterial cells are incubated with the SMA at approximately 37° C.

9. The method of claim 1, wherein the bacterial cells are a Gram-negative bacterial species.

10. The method of claim 9, wherein the Gram-negative bacterial species is selected from the group consisting of *Escherichia. coli, Salmonella* sp., *Pseudomonas fluorescens, Shigella* sp., *Yersinia* sp. and *Klebsiella* sp.

11. The method of claim 1, wherein the incubating step comprises: (i) preparing a population of bacterial cells; (ii) suspending the bacterial cells in a solution containing SMA having a styrene: maleic acid ratio of approximately 2:1 and at a concentration of approximately 2-2.5%; and (iii) incubating the bacterial cells in the solution for approximately 2 hours at approximately 37° C.

12. The method of claim 1, wherein the solution is substantially free of ethylene diamine teteraacetic acid (EDTA).

13. The method of claim 1, wherein the solution contains 50 mM TRIS at pH 8.0 in 0.5 M NaCl.

14. The method of claim 1, further comprising exposing the cells to an osmotic shock.

15. The method of claim 1, further comprising recovering at least a proportion of one component, said component selected from oligosaccharides, amino acids, peptides and various small molecules, of the periplasmic space from the solution.

16. The method of claim 1, wherein the periplasmic space contains recombinant polypeptide.

17. The method of claim 16, wherein the method comprises recovering at least a proportion of recombinant polypeptide from the solution.

18. A method for releasing the content of the periplasmic space of bacterial cells comprising incubating the bacterial cells in a solution containing styrene maleic acid copolymer (SMA) so as to specifically disrupt the outer membrane of the bacterial cells in order to release the content of the periplasmic space without disrupting the inner membrane, such that the content of the periplasmic space is released,
 wherein the SMA is at a concentration of between 0.5-4.5% and the bacterial cells are selected from the group consisting of *Escherichia coli, Salmonella* sp., *Pseudomonas fluorescens, Shigella* sp., *Yersinia* sp., or *Klebsiella* sp., and
 wherein the method comprises a further step of separating spheroplasts from the solution.

\* \* \* \* \*